(12) United States Patent
Chinnayelka et al.

(10) Patent No.: US 9,354,226 B2
(45) Date of Patent: May 31, 2016

(54) TRANSDERMAL SYSTEMS, DEVICES, AND METHODS TO OPTICALLY ANALYZE AN ANALYTE

(75) Inventors: Swetha Chinnayelka, Derry, NH (US); Paul Ripley, Nanuet, NY (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 179 days.

(21) Appl. No.: 13/515,678

(22) PCT Filed: Dec. 16, 2010

(86) PCT No.: PCT/US2010/060774
§ 371 (c)(1),
(2), (4) Date: Jun. 13, 2012

(87) PCT Pub. No.: WO2011/075575
PCT Pub. Date: Jun. 23, 2011

(65) Prior Publication Data
US 2012/0258467 A1     Oct. 11, 2012

Related U.S. Application Data

(60) Provisional application No. 61/287,485, filed on Dec. 17, 2009.

(51) Int. Cl.
*A61B 5/00* (2006.01)
*G01N 33/52* (2006.01)
(Continued)

(52) U.S. Cl.
CPC .............. *G01N 33/52* (2013.01); *A61B 5/1451* (2013.01); *A61B 5/1455* (2013.01);
(Continued)

(58) Field of Classification Search
CPC .......... A61B 5/14532; A61B 5/14546; A61B 5/1486; A61B 5/1455; A61B 5/1495; A61B 5/14514; A61B 5/1411; A61B 5/14; A61B 5/145; A61B 5/1451; A61B 5/1477; A61B 2560/0223; A61B 10/0045; A61B 2010/008; C12Q 1/006; C12Q 1/54; G01N 33/66; G01N 33/53; G01N 33/582; G01N 2021/7786; G01N 21/01; G01N 21/64; G01N 2400/00; G01N 2458/00; G01N 27/40; A61M 2037/0007; A61M 2037/0061; A61M 37/0092; B01L 2300/0887; B01L 3/5023
USPC ......... 600/347, 365, 309, 316, 317, 310, 362, 600/300, 319, 357, 573
See application file for complete search history.

(56) References Cited

U.S. PATENT DOCUMENTS 5,262,035 A    11/1993   Gregg et al.
5,264,104 A    11/1993   Gregg et al.
(Continued)

FOREIGN PATENT DOCUMENTS

WO    WO 00/16099    3/2000
WO    WO 00/59371    10/2000
(Continued)

OTHER PUBLICATIONS

Kost et al., "Transdermal monitoring of glucose and other analytes using ultrasound," Nature Med., 6: 347-350, 2000.
(Continued)

*Primary Examiner* — Erik B Crawford
(74) *Attorney, Agent, or Firm* — Dugan & Dugan, PC

(57) ABSTRACT

The invention provides transdermal optical analysis systems, test sensors, methods, and kits for determining the presence and/or concentration of at least one analyte in a fluid sample. The system includes a transdermal test sensor including an aqueous material including at least one analyte selective reagent and at least one optically active moiety. The optical system preferably uses fluorescent spectroscopy to correlate fluorescent emission or adsorption from a dye with the analyte concentration of the sample. An optical light source and/or detector may be housed with the aqueous material in a housing or external to the housing of the aqueous material.

14 Claims, 8 Drawing Sheets

(51) Int. Cl.
*A61B 5/145* (2006.01)
*A61B 5/1455* (2006.01)
*G01N 33/542* (2006.01)
*G01N 33/66* (2006.01)
*G01N 33/92* (2006.01)

(52) U.S. Cl.
CPC ........ *A61B 5/14532* (2013.01); *A61B 5/14546* (2013.01); *G01N 33/542* (2013.01); *G01N 33/66* (2013.01); *G01N 33/92* (2013.01)

(56) References Cited

U.S. PATENT DOCUMENTS

| | | | |
|---|---|---|---|
| 5,264,105 A | 11/1993 | Gregg et al. | |
| 5,393,615 A | 2/1995 | Corey et al. | |
| 5,498,542 A | 3/1996 | Corey et al. | |
| 5,517,313 A | 5/1996 | Colvin | |
| 5,520,786 A | 5/1996 | Bloczynski et al. | |
| 5,593,852 A | 1/1997 | Heller et al. | |
| 5,899,855 A | 5/1999 | Brown | |
| 5,918,603 A | 7/1999 | Brown | |
| 5,965,380 A | 10/1999 | Heller et al. | |
| 6,071,391 A | 6/2000 | Gotoh et al. | |
| 6,103,033 A | 8/2000 | Say et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,284,478 B1 | 9/2001 | Heller et al. | |
| 6,299,757 B1 | 10/2001 | Feldman et al. | |
| 6,329,161 B1 | 12/2001 | Heller et al. | |
| 6,338,790 B1 | 1/2002 | Feldman et al. | |
| 6,393,318 B1 | 5/2002 | Conn et al. | |
| 6,461,496 B1 | 10/2002 | Feldman et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,560,471 B1 | 5/2003 | Heller et al. | |
| 6,565,509 B1 | 5/2003 | Say et al. | |
| 6,591,125 B1 | 7/2003 | Buse et al. | |
| 6,592,745 B1 | 7/2003 | Feldman et al. | |
| 6,594,514 B2 | 7/2003 | Berner et al. | |
| 6,605,200 B1 | 8/2003 | Mao et al. | |
| 6,605,201 B1 | 8/2003 | Mao et al. | |
| 6,616,819 B1 | 9/2003 | Liamos et al. | |
| 6,618,934 B1 | 9/2003 | Feldman et al. | |
| 6,676,816 B2 | 1/2004 | Mao et al. | |
| 6,749,740 B2 | 6/2004 | Liamos et al. | |
| 6,835,184 B1 | 12/2004 | Sage et al. | |
| 6,893,545 B2 | 5/2005 | Gotoh et al. | |
| 6,931,327 B2 | 8/2005 | Goode et al. | |
| 6,932,894 B2 | 8/2005 | Mao et al. | |
| 6,942,518 B2 | 9/2005 | Liamos et al. | |
| 6,973,706 B2 | 12/2005 | Say et al. | |
| 6,990,366 B2 | 1/2006 | Say et al. | |
| 7,003,341 B2 | 2/2006 | Say et al. | |
| 7,066,884 B2 | 6/2006 | Custer et al. | |
| 7,074,308 B2 | 7/2006 | Mao et al. | |
| 7,090,756 B2 | 8/2006 | Mao et al. | |
| 7,226,978 B2 | 6/2007 | Tapsak et al. | |
| 7,276,029 B2 | 10/2007 | Goode et al. | |
| 7,299,082 B2 | 11/2007 | Feldman et al. | |
| 2002/0151772 A1 | 10/2002 | Polak | |
| 2002/0182658 A1* | 12/2002 | Polak et al. | 435/7.92 |
| 2002/0193672 A1* | 12/2002 | Walsh et al. | 600/316 |
| 2004/0236268 A1 | 11/2004 | Mitragotri et al. | |
| 2004/0259270 A1 | 12/2004 | Wolf | |
| 2005/0064529 A1* | 3/2005 | Kwon | 435/14 |
| 2006/0094946 A1 | 5/2006 | Kellogg et al. | |
| 2007/0179373 A1 | 8/2007 | Pronovost | |

FOREIGN PATENT DOCUMENTS

| | | |
|---|---|---|
| WO | WO 03/052413 | 6/2003 |
| WO | WO 2004/044557 | 5/2004 |
| WO | WO 2004/113893 | 12/2004 |
| WO | WO 2008/109739 | 9/2008 |
| WO | WO 2011/075575 | 6/2011 |
| WO | WO 2011/084607 | 7/2011 |

OTHER PUBLICATIONS

Baker, R.W., "Membrane Technology", Encyclopedia of Polymer Science and Technology, John Wiley & Sons, 184-249, 2001.
Hanot, H. et al., "Expanding the use of track-etched membranes", IVD Technology, p. 41ff, Nov. 2002.
International Search Report of International Application No. PCT/US2010/060786 mailed Apr. 20, 2011.
Written Opinion of International Application No. PCT/US2010/060786 dated Jun. 17, 2012.
International Preliminary Report on Patentability of International Application No. PCT/US2010/060786 dated Jun. 19, 2012.
International Search Report of International Application No. PCT/US2010/060774 mailed Feb. 28, 2011.
Written Opinion of International Application No. PCT/US2010/060774 dated Jun. 17, 2012.
International Preliminary Report on Patentability of International Application No. PCT/US2010/060774 dated Jun. 19, 2012.

* cited by examiner

Glucose + O$_2$ $\xrightarrow{\text{Glucose Oxidase}}$ H$_2$O$_2$ + δ − gluconolactone

TRANSDERMAL SYSTEMS, DEVICES, AND METHODS TO OPTICALLY ANALYZE AN ANALYTE

REFERENCE TO RELATED APPLICATIONS

This application claims the benefit of U.S. Provisional Application No. 61/287,485 entitled "Transdermal Systems, Devices, and Methods to Optically Analyze an Analyte" filed Dec. 17, 2009, which is incorporated by reference in its entirety.

BACKGROUND

The quantitative determination of analytes in biological fluids is important in the diagnosis and maintenance of certain physiological abnormalities. For example, lactate, cholesterol, and bilirubin should be monitored in certain individuals. In particular, determining glucose concentrations in biological fluids is important to diabetic individuals who must regulate the glucose intake of their diets. The results of such tests may be used to determine what, if any, insulin or other medication should be administered.

In some existing technologies, a lancet is used to pierce a user's skin to draw a biological fluid sample, such as blood. This sample is then analyzed with a test sensor external to the skin to determine the concentration of analyte, such as glucose, in the sample. Piercing a user's skin each time an analyte concentration reading is desired is an inconvenient and invasive procedure. Moreover, the procedure is undesirable due to the pain and discomfort experienced by the user.

In other existing technologies, an implant, as described in U.S. Pat. No. 5,517,313 may be placed under the skin. In addition to patient discomfort from the implant placement procedure and healing process, immune system responses may affect the usefulness of the implant differently for individual patients. Thus, implantable sensors may not be useful for some patients.

Conventional non-invasive methods for obtaining a biological fluid sample typically involve extracting a sample of interstitial fluid (ISF) containing the analyte to the surface of the skin for analysis. Transport of the ISF may be accomplished electrically through iontophoresis or by enlarging and/or creating pores through the stratum corneum of the skin. As the sample moves from the epidermal layer of the skin, through the stratum corneum, and to the skin surface, such methods may be referred to as "transdermal." Transdermal methods may be preferred to invasive methods, as patient discomfort and immune system complications are substantially reduced. Transdermal methods also include techniques in which the sample moves through tissues other than skin, such as mucosal tissues, to reach the test sensor.

In transdermal systems relying on iontophoresis, electricity flowing between a pair of electrodes transports ISF to the skin surface for analysis. An example of a transdermal iontophoresis system may be found in U.S. Pat. No. 6,393,318. A commercial transdermal system based on iontophoresis was the GlucoWatch® G2 Biographer (Animas® Corporation; West Chester, Pa.). A disadvantage of iontophoretic sensor systems is that the user's skin may be irritated by the current flowing between the electrodes.

In poration or microporation transdermal methods, small holes or pores are made through the stratum corneum of the skin to a desired depth to lessen the barrier properties of the skin to the passage of biological fluids, such as ISF. Preferably, such pores are about 1 mm or less in average diameter. A transdermal test sensor placed on the surface of the user's porated skin receives the fluid from the pores. Sonication, tiny needles, and other methods are known to porate the skin, thereby enhancing fluid flow to the surface of the skin.

When the fluid reaches the skin surface, it is typically trapped by the reservoir and/or absorptive material of the transdermal test sensor. The test sensor may include a hydrogel or other aqueous material to facilitate the extraction of the fluid from the user's skin to the electrodes of the test sensor. Conventional transdermal electrochemical test sensor designs relying on hydrogels, such as the sensor of the GlucoWatch® system, have disadvantages including interference and delayed diffusion of by-products to the electrode surface caused by the viscosity of the hydrogel, relatively long delays between application of the hydrogel to the skin and useful analysis, relatively high levels of background signal, as well as contamination complications resulting from diffusion of hydrogen peroxide to the electrodes.

The measurement performance of a biosensor system, such as a transdermal sensor system, typically is defined in terms of accuracy and/or precision. Accuracy may be expressed in terms of bias of the sensor system's analyte reading in comparison to a reference analyte reading, with larger bias values representing less accuracy. Precision may be expressed in terms of the spread or variance of the bias among multiple analyte readings in relation to a mean. It would be desirable to increase the accuracy and/or precision of transdermal sensor systems, to provide for an improvement in measurement performance.

Bias is the difference between one or more analyte concentration values determined from the biosensor system, and one or more accepted reference values for the analyte concentration in the biological fluid. Thus, one or more errors of a biosensor system in its analysis can result in a bias of the analyte concentration determined from the system. Bias may be expressed in terms of "absolute bias" in the units of the measurement such as mg/dL, or in terms of "percent bias" as a percentage of the absolute bias value over the reference value. Under the ISO standard for glucose measurements, absolute bias is used to express error in glucose concentrations less than 75 mg/dL, while percent bias is used to express error in glucose concentrations of 75 mg/dL and higher. Accepted reference values for analyte concentrations may be obtained with a reference instrument, such as the YSI 2300 STAT PLUS™ available from YSI Inc., Yellow Springs, Ohio.

Accordingly, it would be desirable to have a transdermal sensor system that assists in addressing one or more of the above disadvantages.

SUMMARY

The invention provides transdermal optical analysis systems, test sensors, methods, and kits for determining the presence and/or concentration of at least one analyte in a fluid sample. The concentration of the at least one analyte may be determined in ISF that has passed through a tissue to reach the aqueous material of the test sensor.

A non-invasive method for determining a concentration of at least one analyte in a fluid includes contacting a test sensor of a transdermal optical analysis system to tissue, the test sensor including an aqueous material and a reagent system; establishing fluid communication between the tissue and the aqueous material; transferring the at least one analyte in the body fluid from the tissue into the aqueous material, the aqueous material including at least one analyte selective reagent and at least one optically active moiety; altering light entering the aqueous material from a source with the at least one optically active moiety in response to the concentration of the at least one analyte in the body fluid; and determining the concentration of the at least one analyte in the body fluid using a measurement device in communication with the test sensor.

A non-invasive method for determining a concentration of at least one analyte in a fluid includes contacting porated tissue with an aqueous material of a transdermal test sensor, the test sensor including the aqueous material and a reagent system; allowing sufficient time for a fluid sample to traverse the porated tissue and enter the aqueous material, the aqueous material including at least one analyte selective reagent and at least one optically active moiety; applying at least one wavelength of light to the aqueous material; detecting at least one wavelength of light from the aqueous material; and correlating the alteration between the applied and detected light with the concentration of the at least one analyte in the sample.

A transdermal optical analysis test system for non-invasively determining the concentration of at least one analyte in a fluid includes a transdermal test sensor and a measurement device. The transdermal test sensor includes a housing at least partially enclosing an aqueous material, the aqueous material including at least one analyte selective reagent and at least one optically active moiety. The at least one analyte selective reagent includes at least one of a receptor and one or more species that the analyte displaces from the receptor, an analyte binding moiety that undergoes a conformation change when contacted by the analyte, an analyte binding moiety that undergoes a change in electron withdrawing ability when contacted by the analyte, and an analyte binding moiety that produces at least one byproduct when contacted by the analyte. The at least one optically active moiety includes at least one of a pH sensitive dye, an oxygen sensitive dye, a donor fluorescent dye and an acceptor fluorescent dye in combination, and a donor fluorescent dye and a quencher in combination. The transdermal test sensor also includes an optical analysis system including a light source and a detector. In combination, the test sensor and the measurement device implement one or more of the previously discussed methods to determine the concentration of the at least one analyte in the fluid. The measurement device may communicate through wires or wirelessly with the test sensor.

A transdermal optical analysis test system for non-invasively determining the concentration of at least one analyte in a fluid includes means for contacting porated tissue with an aqueous material of a transdermal test sensor, means for allowing a fluid sample to traverse the porated tissue and enter the aqueous material, means for applying at least one wavelength of light to the aqueous material, means for detecting at least one wavelength of light from the aqueous material, and means for correlating the alteration between the applied and detected light with the concentration of the at least one analyte in the sample.

A transdermal optical analysis test sensor for non-invasively determining the concentration of at least one analyte in a fluid includes a housing at least partially enclosing an aqueous material. The aqueous material includes at least one analyte selective reagent and at least one optically active moiety. The at least one analyte selective reagent includes at least one of a receptor and one or more species that the analyte displaces from the receptor, an analyte binding moiety that undergoes a conformation change when contacted by the analyte, an analyte binding moiety that undergoes a change in electron withdrawing ability when contacted by the analyte, and an analyte binding moiety that produces at least one byproduct when contacted by the analyte. The at least one optically active moiety includes at least one of a pH sensitive dye, an oxygen sensitive dye, a donor fluorescent dye and an acceptor fluorescent dye in combination, and a donor fluorescent dye and a quencher in combination. The test sensor also includes an optical analysis system including a light source and a detector that may reside internal or external to the housing. The aqueous material may adhere to the tissue of an organism.

A kit may include the transdermal optical analysis test system. A refill kit may include the transdermal optical analysis test sensor.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Figure 1A:
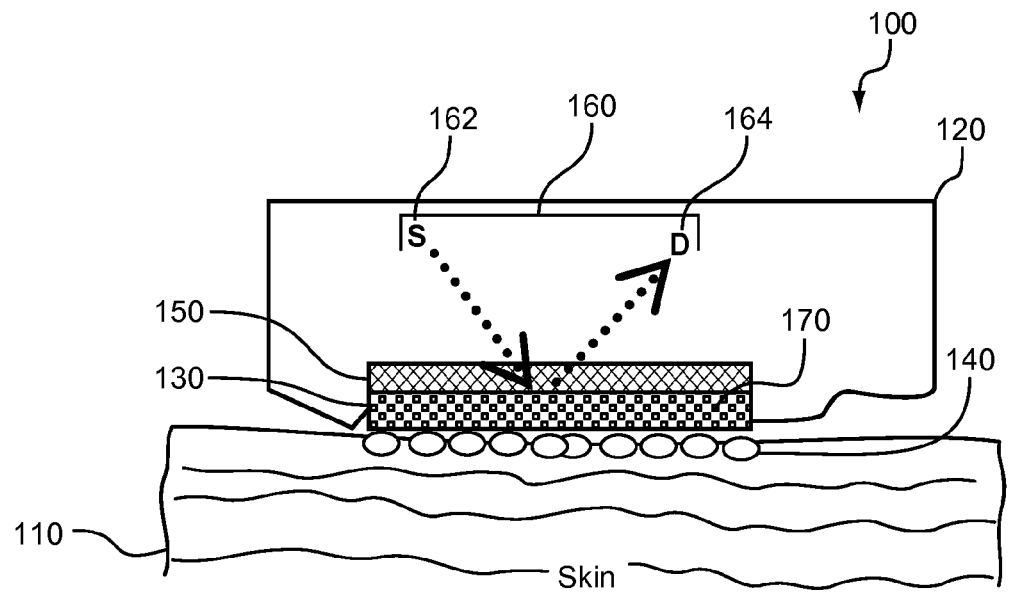
FIG. 1A is a schematic of an optically read transdermal test sensor.

A transdermal optical analysis system uses a transdermal test senor including an aqueous material and a reagent system, and an optical analysis system to analyze for at least one analyte in a sample. The reagent system includes at least one analyte selective reagent and preferably at least one optically active moiety in an aqueous material. At least one light source and at least one detector are incorporated with the test sensor or provided external to the test sensor. One or more components of the reagent system interact with the analyte to alter the light received by the detector. A measurement device correlates the signal obtained from the detector with the analyte concentration of the sample.

In relation to conventional electrochemical transdermal systems, which require a long electrode conditioning period before analysis may be performed, the described transdermal optical analysis systems may analyze the sample as soon as sufficient analyte reaches the aqueous material. The optical analysis systems may perform an analyte analysis within 2 hours of being adhered to the tissue. Some conventional electrochemical transdermal systems require more than one hour of conditioning before analysis may be performed. Preferably, the optical analysis systems can perform an analyte analysis within 50 minutes, 40 minutes, 30 minutes, 20 minutes or less of being adhered to the tissue. More preferably, the optical analysis systems can perform the analyte analysis within 15 minutes or less of being adhered to the tissue.

The transdermal optical analysis systems also may provide more precise concentration values over a wider range of aqueous material hydration in relation to conventional electrochemical hydrogel-based systems. Increases in signal-to-noise ratios for the transdermal optical analysis systems also may be observed by contacting the aqueous material with the light source or by incorporating the light source into the aqueous material.

Conventional electrochemical transdermal systems continuously apply current to the test sensor electrodes, due at least in part to the electrode conditioning period. This continual current application to the test sensor requires significant battery power and heavier duty circuits, and may result in more rapid hydrogel dehydration and the associated failure of the test sensor. Lacking analyte analysis electrodes and the associated constant "on" operation of electrochemical transdermal test sensors, the described transdermal optical analysis systems provide a significant advantage as power is only required when the optical analysis system is activated. Thus, intermittent operation can substantially reduce the battery requirements of a transdermal optical analysis system in relation to a conventional electrochemical system. Furthermore, the ability to maintain sufficient aqueous material hydration for longer periods may be enhanced in relation to conventional electrochemical systems by removing current flow from the system, thus increasing the operational life of the test sensor.

In relation to conventional electrochemical test sensors, the described transdermal optical analysis systems may reduce the accuracy problems resulting from one or more interferants in the sample. Sample interferants in electrochemical systems are chemical, electrochemical, physiological or biological species that result in a positive or negative bias in the electrochemically determined analyte concentration. Compensation for inaccuracies due to sample interferants in conventional electrochemical test sensors typically requires a separate electrode or electrode system to quantify each interferant, which in turn requires additional processing by the measurement device to remove the contribution of the interferant from the measured analyte concentration. An optical analysis system can avoid these complications by using a reagent system that is highly specific to the analyte.

In relation to conventional electrochemical transdermal test sensors, the described transdermal optical analysis systems may reduce the accuracy problems resulting from an electrochemically active species, such as $H_2O_2$, diffusing through a hydrogel. In electrochemical transdermal test sensors, hydrogels can lead to inaccuracy. This inaccuracy may be attributed to the varying diffusion kinetics of the electrochemically active species traveling through the hydrogel to the electrodes. As the diffusion rate of the electrochemically active species to the electrode is correlated with analyte concentration in these systems, any variance in diffusion rate not attributable to analyte concentration results in measurement inaccuracies.

FIG. 1A represents a transdermal optical analysis test sensor 100 including a housing 120 at least partially enclosing an aqueous material 130 in contact and fluid communication with tissue 110 at least through porated region 140. An optical screen 150 optionally separates the aqueous material 130 from at least a portion of analyzer 160, which includes at least one source 162 and at least one detector 164. The source 162 and/or the detector 164 optionally may include one or more light altering device, such as filters and the like. The test sensor 100 includes a reagent system 170, preferably at least partially residing in the aqueous material 130. The aqueous material 130 may self-adhere to the tissue 110, or may be adhered with one or more adhesives (not shown). While a particular configuration is shown, the test sensor 100 may have other configurations, including those with additional components.

The test sensor 100 may be placed on any surface of a body where sufficient biological fluid may be obtained for analysis, such as on the volar forearm between the wrist and the elbow. While "skin" is typically used to describe the tissue with which the test sensor 100 is in fluid communication, the sensor 100 may be in fluid communication with any tissue type suitable for passing an analyte for analysis, such as mucosal, muscle, and organ.

The test sensor 100 may be used to determine the concentration of one or more analytes in a biological fluid, such as ISF, residing on the other side of the tissue from the test sensor 100. Examples of analytes include, but are not limited to, glucose, lactate, glutamate, cholesterol, calcium, urea, triglycerides, high density lipoprotein (HDL), low density lipoprotein (LDL), bilirubin, fructosamine, and hematocrit. For example, the test sensor 100 may be used to determine the glucose concentration in ISF drawn through the forearm skin. In addition to glucose, the test sensor 100 may optionally determine the concentration of another analyte. In another example, the test sensor 100 may be used to determine the concentration of one or two non-glucose analytes in the sample. ISF is the preferred sample, although other biological fluids also may be used.

The test sensor 100 may be used to determine the concentration of one or more analytes while residing on the surface of the body for an extended time period. The extended time period may extend up to one day. Preferably the extended time period extends up to 2 days, up to 3 days, up to 5 days, up to one week, and preferably may extend longer than one week.

During this extended time period the reagent system 170 of the test sensor 100 may be optically read continuously or intermittently. Preferably, the reagent system 170 is intermittently read at least once every 1 to 2 minutes, at least once every 2 to 4 minutes, at least every 4 to 6 minutes, at least every 6 to 10 minutes, and at least once every 10 to 20 minutes. Longer time periods, such as at least once every hour, at least once every 12 hours, at least once a day, at least once a week, at least once every 2 weeks, and at least once every month also may be used.

The test sensor 100 may be used to determine the concentration of one or more analytes when desired by a user. The test sensor 100 may be placed on the surface of the body, the reagent system 170 may be read, and then the test sensor may be removed from the surface of the body. In this arrangement, the test sensor 100 may be used only once, or it may be used more than once. For example, after the test sensor 100 has been used to determine the concentration of one or more analytes, it may be removed from the surface of the body and stored for future use, such as by sealing it and/or placing the aqueous material of the sensor in contact with a solution. The same test sensor may then be used to determine the concentration of one or more analytes again at a later time.

Figure 1B:
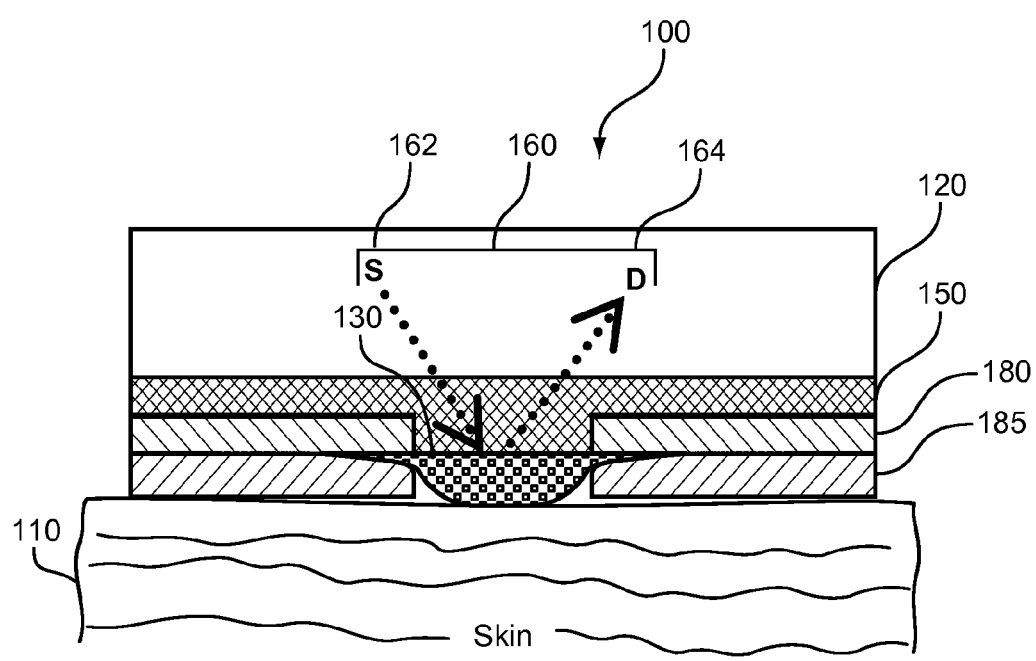
FIG. 1B is another schematic of an optically read transdermal test sensor.

The housing 120 may be made from any material and in any shape compatible with the other components of the test sensor 100 and the analysis. The housing 120 assists in keeping the aqueous material 130 in fluid communication with the porated region 140 of the tissue 110 and in optical communication with the optical analyzer 160. For example, FIG. 1B represents a transdermal optical analysis test sensor 100 where the aqueous material 130 is held between a top adhesive 180 and a bottom adhesive 185. The bottom adhesive 185 adheres the test sensor 100 to the tissue 110.

The aqueous material 130 serves as an interface between the optical analyzer 160 and the porated region 140 of the tissue. The aqueous material 130 may enhance the flow of fluid from the tissue 110 to the test sensor 100 by maintaining a diffusive path between the fluidic interior of the organism and the test sensor 100.

The aqueous material 130 may be a hydrogel that includes water and one or more polymeric materials, such as a prepolymer, a polymer, or a combination thereof. The hydrogel also may include a solvent, which is preferably substantially biocompatible with the tissue. The hydrogel includes water, and may further include one or more buffers, organic solvents, surfactants, dispersants, viscosity modifiers, and the like. The polymeric material or materials forming the hydrogel preferably satisfy three properties: (i) preferably, they should be substantially free of light scattering in the wavelength region used by the optical analyzer 160, (ii) preferably, they should have good hydration properties, that is, they should retain a substantial water content throughout the analysis, and (iii) preferably, they should have an affinity for adhering to the tissue.

Suitable polymeric materials for use in a hydrogel 130 include, but are not limited to, polyethylene oxide (PEO), polyvinyl alcohol (PVA), polyethylene glycol diacrylate (PEGDA), polyvinyl pyrrolidone (PVP), agarose, polyacrylamide, gelatin, nafion, vinyl acetate, polyethyleneimine (PEI), polyhydroxyethyl methacrylate (poly-HEMA), polyethylene glycol dimethacrylate (poly-EGDMA), polyurethanes functionalized or modified with amines and/or other hydrophilicity enhancing groups or modifiers, and combinations and derivatives thereof. Presently preferred polymeric materials for use with test sensor 100 include PVA, PEO, polyurethanes functionalized or modified with amines and/or other hydrophilicity enhancing groups or modifiers, and combinations of PVP with vinyl acetate. More preferred combinations of PVP with vinyl acetate include about a 3 to 1 ratio of PVP to vinyl acetate by weight/weight (w/w).

Depending on the polymeric material or materials used, a hydrogel 130 is preferably formed from a mixture including from about 10% to about 99% water to polymeric materials (w/w). More preferably, the hydrogel is formed from a mixture including from about 50% to about 95% water to polymeric materials (w/w). The preferred amount of water in the polymeric material may vary depending on the polymeric material amount, as well as on the characteristics of the polymeric material. For example, the degree of cross-linking can alter the weight of water the hydrogel can hold.

For PVA and PEO, mixtures including from 90% to 95% water to polymeric materials (w/w) are more preferred. For polyurethanes functionalized or modified with amines and/or other hydrophilicity enhancing groups or modifiers, mixtures including from 93% to 97% water to polymeric materials (w/w) are more preferred. For some polymeric materials, such as combinations of PVP with vinyl acetate, an additional solvent may not be needed to form the polymeric material. Once formed, excess monomer may be removed and the polymeric material may be hydrated before incorporation into the test sensor 100. In one example, a hydrogel may be formed from a mixture including 6 mL of 1-vinyl-2-pyrrolidinone, 4 mL of vinyl acetate, 50 microliters of diethylene glycol divinyl ether as a cross-linker, and 50 mg of 1-[4-(2-hydroxyethoxy)-phenyl]-2-hydroxy-2-methyl-1-propane-1-one (Irgacure2959) as a photoinitiator. In this example, the hydrogel may be formed in the presence of a plastic net to ensure adequate physical support for the gel.

The aqueous material 130 may include an aqueous liquid and a semipermeable membrane. Preferably the housing 120 includes an opening, and the semipermeable membrane is connected to the housing and covers the opening. The housing 120 and the semipermeable membrane in combination enclose the aqueous liquid. Examples of aqueous materials including an aqueous liquid and a semipermeable membrane are described, for example in U.S. Provisional Patent Application No. 61/287,509 entitled "Transdermal Systems, Devices, and Methods for Biological Analysis," with inventors Jiangfeng Fei et al., filed Dec. 17, 2009.

The semipermeable membrane of the aqueous material 130 may include any material that allows the analyte to enter the aqueous liquid, but that substantially prevents loss of the aqueous liquid from the test sensor 100. Examples of semipermeable membrane materials include cellulose, cellulose ester such as ethyl cellulose, polypropylene, polyester, polycarbonate, polyamide, polysulfone, poly(vinylidene fluoride), polyimide and polyetherimide. The semipermeable membrane also may include an adhesive, such as an adhesive for attaching the semipermeable membrane to the tissue 110. Preferably, the semipermeable membrane has a hydrophilic surface, having a water contact angle less than 45°. In one example, the semipermeable membrane may include a semipermeable substrate and a hydrophilic layer on at least a portion of the semipermeable substrate. Preferably, the pores of the semipermeable membrane are large enough to permit an analyte to pass from the biological fluid sample to the aqueous liquid, yet are small enough to minimize the loss of the aqueous liquid and/or the reagent system 170 from the test sensor 100.

The semipermeable membrane of the aqueous material 130 may include, for example, a porous polycarbonate substrate and a surface layer of poly(vinyl pyrrolidone) (PVP) on the substrate. The semipermeable membrane of the aqueous material 130 may include, for example, a track-etched membrane having a narrow range of pore diameters. In a specific example, the semipermeable membrane may include a track etched polycarbonate membrane having a PVP surface layer and a 50 nm maximum pore diameter.

The aqueous liquid of the aqueous material 130 may provide a medium in which the analyte and the reagent system 170 can interact to produce a measurable species that is measured by the optical analyzer 160. Preferably the aqueous liquid includes an aqueous buffer. The viscosity of the aqueous liquid may be from 0.01 to 1 poise.

The reagent system 170 is responsive to the desired analyte, while the optical analyzer 160 detects and/or quantifies the change in the reagent system 170 responsive to the analyte. The reagent system 170 is capable of a measurable change in the presence of the desired analyte. The change is optically measured by the alteration of at least one light beam and may be observed through any known spectroscopic technique compatible with the sample, the test sensor 100, and the reagent system 170. The change may be observed from the alteration of at least one light beam in response to an interaction between the analyte and the reagent system 170. The change also may be observed from the alteration of at least one light beam in response to one or more optically-active molecules responsive to an interaction between the analyte and the reagent system 170. While the terms "fluorescent dye" or "dye" are generally used in this application to describe optically-active molecules, it is to be understood that in addition to dyes, any species may be used that absorbs and/or emits at desirable wavelengths and is compatible with the test sensor 100 and the sample, including quantum dots, nanocrystals, reactive chemicals and the like. At present, fluorescent dyes are preferred as optically-active molecules.

Preferred reagents for inclusion in the reagent system 170 include enzymes that are substantially specific to an analyte or analyte by-product and/or analyte binding moieties that substantially bind with an analyte or analyte by-product. The enzymes and/or analyte binding moieties may be physically trapped in the aqueous material 130 or chemically attached to the aqueous material 130. One or more reagents of the reagent system 170 also may reside external to the aqueous material 130 when the test sensor 100 is formed and/or during use. For example, the test sensor 100 may be equipped with a port allowing for additional reagent to be added before and/or during use. In another example, the test sensor 100 may include an additional membrane between the aqueous material 130 and the interior of the housing 120 to reduce fluid communication between the aqueous material 130 and the optical analyzer 160.

By changing the reagent system 170, the concentration and/or presence of analytes, such as cholesterol, glutamate, and lactate, may be determined. For fluorescence resonance energy transfer (FRET) and antibody/analog based detection systems, such as for cholesterol, an increase in cholesterol concentration should be reflected in a decrease in FRET from the antibody/analog system, thus an anti-cholesterol antibody may be paired with an analog, such as 22-(N-(7-nitrobenz-2-oxa-1,3-diazol-4-yl)amino)-23,24-bisnor-5-cholen-3β-ol, fluoresterol, NBD-cholesterol, and the like. For glutamate, an anti-glutamate antibody may be paired with an analog, such as glutamate dimethyl ester, alpha-aminomethylglutarate, and the like. For lactate, an anti-lactate antibody may be paired with an analog, such as benzoylformate and the like. Analogs for these and other analytes also may be made by designing appropriate molecular imprinted polymers. For enzyme based systems, such as one using lactate oxidase to produce lactic acid in the presence of lactate, the resulting change in the pH of the sample may be measured.

Enzymes for use in the reagent system 170 for glucose analysis include glucose oxidase (GOx), glucose dehydrogenase (GDH), hexokinase, glucokinase, and the like. In the presence of glucose, these enzymes release reaction by-products that may be detected with the appropriate optically-active dye or dyes. In enzymatic reactions, the dissociation constant ($K_d$) is fixed, therefore, enzymes for use in the reagent system 170 are preferably selected in response to the required physiological range of the analyte expected to enter the aqueous material 130. For example, when the analyte is glucose contained in ISF that travels through porated tissue to reach the aqueous material 130, the physiological concentration of glucose in the ISF is preferably from 0 to 600 micromolar (μM) before the ISF reaches the aqueous material 130. More preferably, the concentration of glucose in the ISF reaching the aqueous material 130 is from 0 to 300 μM. At present, glucose concentrations of from 0 to 200 μM are most preferred in the ISF reaching the aqueous material 130.

Glucose binding moieties for use in the reagent system 170 for glucose analysis include glucose binding protein, boronic acids with a high affinity for glucose, concanavalin A (Con A), and apoenzymes. In the presence of glucose, these binding moieties undergo a conformational or electronic change that may be detected with the appropriate optically-active dye or dyes. In competitive binding reactions, $K_d$ can be adjusted by varying the receptor to ligand concentration ratio, and thus the sensitivity can be tailored in the range of analyte concentrations expected to enter the aqueous material 130.

Fluorescent dyes may be used in the reagent system 170 and may be physically trapped or chemically attached to the aqueous material 130 and/or one or more of the reagents of the reagent system 170. The reagent system 170 may include one or more dyes that undergo a measurable change in response to the surrounding pH or surrounding oxygen concentration. The reagent system 170 may include one or more dyes that undergo a measurable change when the distance between two dyes change. The reagent system 170 may include one or more dyes that undergo a measurable change when the functional groups of surrounding moieties having the closest proximity to the dyes change. The reagent system 170 also may include one or more reference dyes that do not undergo a measurable change in response to the analysis.

The range of analyte concentrations that the test sensor 100 may detect in a sample may be increased in multiple ways. For reagent systems using enzymes, the detectable analyte concentration range may be increased by using one enzymatic reaction and different dyes to measure different pH ranges. For example, Table I, below, shows that green, orange, and red dyes may measure glucose concentrations in ISF in the range of 0-20 mM, 20-40 mM, and 40-60 mM, respectively. Thus, the green dye would alter light at higher pH values, while the red dye would alter light at lower pH values, reflecting lower and higher glucose concentrations, respectively.

TABLE I

|  | Glucose | | |
| --- | --- | --- | --- |
|  | 0-20 mM | 20-40 mM | 40-60 mM |
| Fluorescent-dye color | Green | Orange | Red |

The operating range of the test sensor 100 also may be increased by using a first enzyme specific to analyte sample concentrations in the micromolar range and a second enzyme specific to analyte sample concentrations in the millimolar range. In this system, analyte concentrations may be determined in both ranges if the first and second enzymes are associated with dyes that alter light differently. Similarly, the concentration of multiple analytes in a sample may be determined using different enzymes, each specific to a different analyte and each associated with a dye that alters light differently. For example, Table II below shows that a green dye is associated with the glucose oxidase enzyme and will absorb or emit light at different green wavelengths depending on the glucose concentration of the sample. By measuring the light alterations in the green, orange, and red wavelengths for the sample, the concentrations of glucose, lactate, and cholesterol may be individually determined.

TABLE II

| Multi-analyte | Glucose | Lactate | Cholesterol |
| --- | --- | --- | --- |
| Enzyme | Glucose Oxidase | Lactate Oxidase | Cholesterol Oxidase |
| Fluorescent-dye color | Green | Orange | Red |

When present, the optical screen 150 protects at least a portion of the optical analyzer 160 from the aqueous material 130 and/or the reagent system 170. The optical screen 150 may be made from any optically transparent material that provides sufficient isolation to the optical analyzer 160, and is chemically compatible with the aqueous material 130, the reagent system 170, and the analyte. Preferable materials from which the optical screen 150 may be made include polycarbonate, polyethylene, polyvinyl chloride (PVC), polyurethane, polyethylene-terephthalate (PET), polyester, thermoset polymers made from allyl diglycol carbonate monomers (such as FOSTA-TEK ADC, Fosta-Tek Optics, Inc., Leominster, Mass., USA), glass, cellulose acetate, polymethyl methacrylate (PMMA), and combinations thereof.

The light source 162, optional optical filters (not shown), and the detector 164 are known in the art, such as described in US 2002/0151772. Examples of preferable devices for use as the light source 162 include light emitting diodes (LEDs), dual LEDs, laser diodes, broadband sources, specific bandwidth LEDs, and the like. Examples of preferable devices for use as the detector 164 include those comprising silicon, silicon avalanche, GaAs photodiodes, and like devices capable of converting light into electricity. For multiple dyes, a broadband source may be used with different optical filters, different wavelength LEDs may be used as the source 162, and the like.

The source 162 and/or the detector 164 may be located within the housing 120 or external and in close proximity to the housing 120 if a portion of the housing 120 is of sufficient transparency for the test sensor 100 to operate suitably. The source 162 and/or the detector 164 also may be located at a remote location from the test sensor 100 and may be in light communication with the reagent system 170 by an optical fiber, light pipe, or the like. The source 162 may reside partially or wholly within the aqueous material 130, thus providing an increase in light energy applied to the dyes. Preferable sources for use within the aqueous material 130 are organic light emitting diodes (OLEDs).

The optical analyzer 160 measures the amount of light absorbed and/or generated by the interaction of the reagent system 170 with the analyte. After being altered by the reagent system, the light from the source 162 is preferably converted into an electrical signal, such as current or potential, by the detector 164.

In light-absorption optical analyses, the reagent system 170 produces a reaction product that absorbs light. An incident excitation beam from the light source 162 is directed toward the aqueous material 130. The incident beam may be reflected back from, or transmitted through, the sample to the detector 164, depending on the placement of the detector 164. The detector 164 collects and measures the attenuated incident beam. The amount of light attenuated by the reaction product is an indication of the analyte concentration in the sample.

In light-generated optical analyses, the reagent system 170 produces a reaction product that fluoresces or emits light in response to the analyte. The detector 164 collects and measures the generated light. The amount of light produced by the reaction product provides an indication of the analyte concentration in the sample.

Figures 2A, 2B:
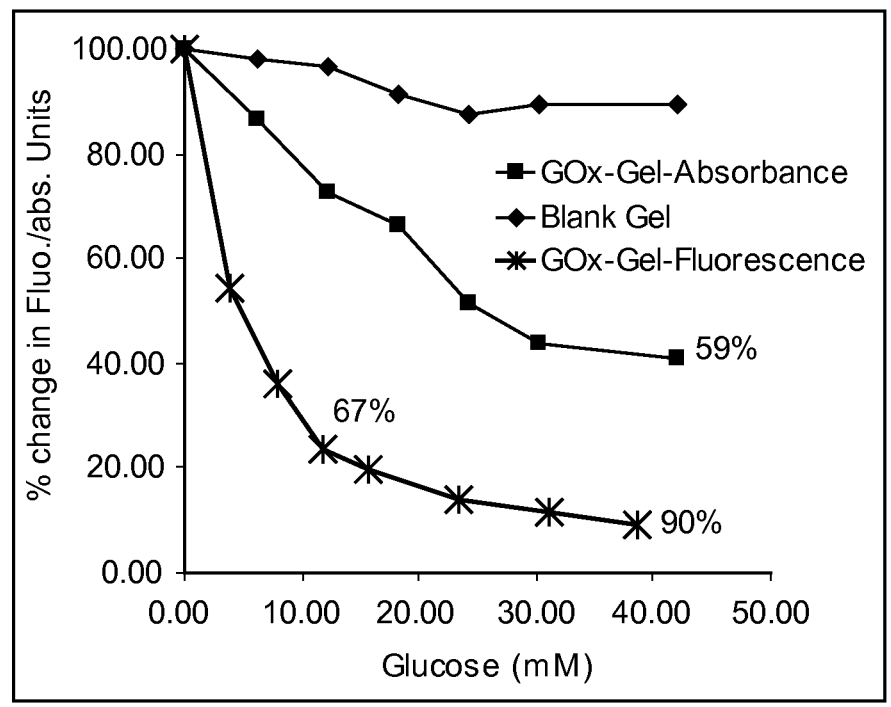
FIG. 2A represents a reaction scheme for an enzymatic reagent system using the glucose oxidase enzyme in combination with pH and/or oxygen sensitive dyes.
FIG. 2B plots percent change in fluorescence or absorbance against glucose concentrations observed in a hydrogel.

FIG. 2A represents a reaction scheme for an enzymatic reagent system using the glucose oxidase enzyme in combination with pH and/or oxygen sensitive dyes. When exposed to glucose, the glucose oxidase enzyme reacts with glucose and oxygen ($O_2$) to produce gluconic acid (gluconolactone), thus lowering the oxygen content and the pH of the sample. pH sensitive dyes alter light in response to changes in pH, while oxygen sensitive dyes alter light in response to changes in oxygen concentration. As the decrease in sample oxygen content and/or pH is responsive to the glucose concentration of the sample, the change in the fluorescent signal or signals observed from the dye or dyes is responsive to the glucose concentration of the sample. In addition to the pH or oxygen sensitive dyes, an internal reference also may be provided by including one or more fluorescent dyes in the reagent system that are not pH or oxygen sensitive.

FIG. 2B plots percent change in fluorescence or absorbance against glucose concentration in millimolar (mM) observed in a hydrogel. The hydrogel lacking a reagent system showed little change in absorbance when different concentrations of glucose were added. When a glucose oxidase (GOx) enzyme and the pH sensitive dye fluorescein isothiocyanate (FITC) were added, the absorbance and fluorescence observed from the hydrogel was responsive to increasing concentrations of glucose. The fluorescence sensitivity was about 3.5 times that of the absorbance measurements. By tuning the amount of enzyme to dye to a molar ratio of 1:2, the linear region of detection was increased to about 30 mM.

The results plotted in FIG. 2B were obtained using a hydrogel prepared from a mixture including 6 mL of 1-vinyl-2-pyrrolidinone, 4 mL of vinyl acetate, 50 microliters of diethylene glycol divinyl ether as a cross-linker, and 50 mg of 1-[4-(2-hydroxyethoxy)-phenyl]-2-hydroxy-2-methyl-1-propane-1-one (Irgacure2959) as a photoinitiator. The hydrogel was formed in the presence of a plastic net to ensure adequate physical support for the gel. The hydrogel was modified to include GOx by crosslinking with a solution containing 5% GOx, 0.5% bovine serum albumin and 2.5% glutaraldehyde.

pH sensitive dyes that may be used with the test sensor 100 include those in Table III, below.

TABLE III

| Parent Fluorophore | pH Range | Typical Measurement |
|---|---|---|
| SNAFL | 6.0-8.2 | Excitation ratio 510/540 nm |
| SNARF indicators | 6.0-8.0 | Emission ratio 580/640 nm |
| FITC | 5.0-8.0 | Emission 520 nm |
| HPTS (pyranine) | 7.0-8.0 | Excitation ratio 450/405 nm |
| BCECF (2',7'-Bis-(2-carboxyethyl)-5-(and-6)-carboxyfluorescein) | 6.5-7.5 | Excitation ratio 490/440 nm |
| Fluoresceins and carboxyfluoresceins | 6.0-7.2 | Excitation ratio 490/450 nm |

When glucose is added to a mixture of glucose oxidase in PBS buffer, the pH of the mixture increases from 7.3 to 7.4. Preferably a pH sensitive dye for use in the test sensor is sensitive to pH changes within this range. Preferred pH sensitive dyes for use in the test sensor include seminaphthorhodafluors (SNAFL), fluorescein isothiocyanate (FITC), and 8-Hydroxypyrene-1,3,6-Trisulfonic Acid (HPTS). The HPTS dye is especially preferred as a pH sensitive dye that provides two fluorescence peaks, the ratio of which may be used as the change responsive to the analyte concentration. In this way, an internal standard may be provided to the optical analyzer without the need of a second dye.

A dye used with the test sensor 100 may include an oxygen sensitive dye. Preferably an oxygen sensitive dye for use in the test sensor is an oxygen sensitive dye including bipyridyl (bpy) groups. Preferred oxygen sensitive dyes include (tris(2, 2'-bipyridyl dichlororuthenium) hexahydrate (Ru(bpy)).

Binding reagent systems rely on the association of an analyte with one or more components of the reagent system and may use one or more optical analysis techniques to determine the separation and/or a change in the separation of two or more dyes. Binding reagent systems also may use optical techniques that determine a change in the electron density surrounding one or more dyes.

FIGS. 3(a) and 3(b) represent a binding reagent system using competitive binding to analyze for the analyte. FIG. 3(a) represents an analyte-specific receptor 310 having an attached first fluorescent dye 320. A ligand 330 having an attached second fluorescent dye 340 is associated with the receptor 310. Preferably, the fluorescent dyes 320, 340 are attached by conjugation to functional groups available on the receptor 310 and the ligand 330, respectively. The fluorescent dyes 320, 340 also may be covalently attached to the receptor 310 and/or the ligand 330, respectively. While not wishing to be bound by any particular theory, the association between the receptor 310 and the ligand 330 is believed attributable to an affinity based mechanism.

As represented in FIG. 3(b), in the presence of the analyte 350, the ligand 330 dissociates from the receptor 310, thus allowing separation of the first and second fluorescent dyes 320, 340. The receptor can be any moiety that retains sufficient specificity to the analyte 350 to provide the desired measurement performance to the analysis. The ligand 330 may be any molecule that can bind to the receptor and has a binding constant lower than that of the analyte 350 to the receptor 310.

The response of the system may be chosen by selecting the dyes attached to the receptor 310 and the ligand 330; by altering the labeling ratio of the dyes attached to the receptor 310 versus the ligand 330; and/or by selecting the concentration ratio of the receptor 310 to the ligand 330. For example, by selecting the specific dyes and/or the labeling ratio of the dyes used with the system, the quantity of light output generated in response to a specific quantity of analyte in the sample may be chosen. Similarly, the sensitivity of the system to a specific analyte may be chosen by selecting the concentration ratio of the receptor 310 to the ligand 330. For glucose analysis, competitive binding reagent systems are preferably configured to detect glucose in ISF at least down to millimolar concentrations. By preferably configuring the dyes, dye ratio, and receptor/ligand ratio, the system can achieve a precision between different assays of ±5%, more preferably ±3%. At present, configurations providing a precision between different assays of ±0.5% are especially preferred.

Fluorescence resonance energy transfer (FRET) can be regarded as the interaction of the transition dipoles of the donor and acceptor dyes. In this phenomenon, when a donor dye is excited at a specific wavelength, the energy is believed to transfer non-radiatively from the donor to an acceptor dye. This transfer occurs when certain criteria are met, including the approximate proximity of the dyes. The distance required between the two dyes for the FRET to occur may depend on multiple factors including the choice of FRET dyes. Preferably, the distance between the donor and acceptor dyes is in the range of about 50 Å to about 100 Å. A suitable distance of about 100 Å or less may be provided between preferable receptors and analogues for the formation of FRET capable pairs. Because of the distance requirement, FRET may be substantially reduced or eliminated when the dyes are freely floating in solution.

To measure the dissociation of the ligand 330 from the receptor 310, the spectroscopic technique of FRET is preferred, as depicted in FIG. 3(c) and in FIG. 3(d). In FIG. 3(c) the complex of the receptor 310 and the ligand 330 form strong donor and acceptor peaks due to considerable resonance energy transfer from the donor to acceptor fluorescent dyes, respectively. Because this energy transfer depends on the distance between the donor and acceptor dyes, when the receptor/ligand complex is exposed to the analyte 350, the ligand 330 is displaced by the analyte 350 from the receptor 310 (due to the greater affinity of the analyte for the receptor).

The displacement of the ligand 330 from the receptor 310 results in increased distance between the first and second fluorescent dyes 320, 340. As the dyes separate, resonance energy transfer decreases, thus providing a detectable decrease in the second fluorescent dye peak 340' relative to the first fluorescent dye peak 320' as shown in FIG. 3(d). The first fluorescent dye peak 320' also may increase as energy previously adsorbed by the second fluorescent dye 340 is detected.

Figure 3:
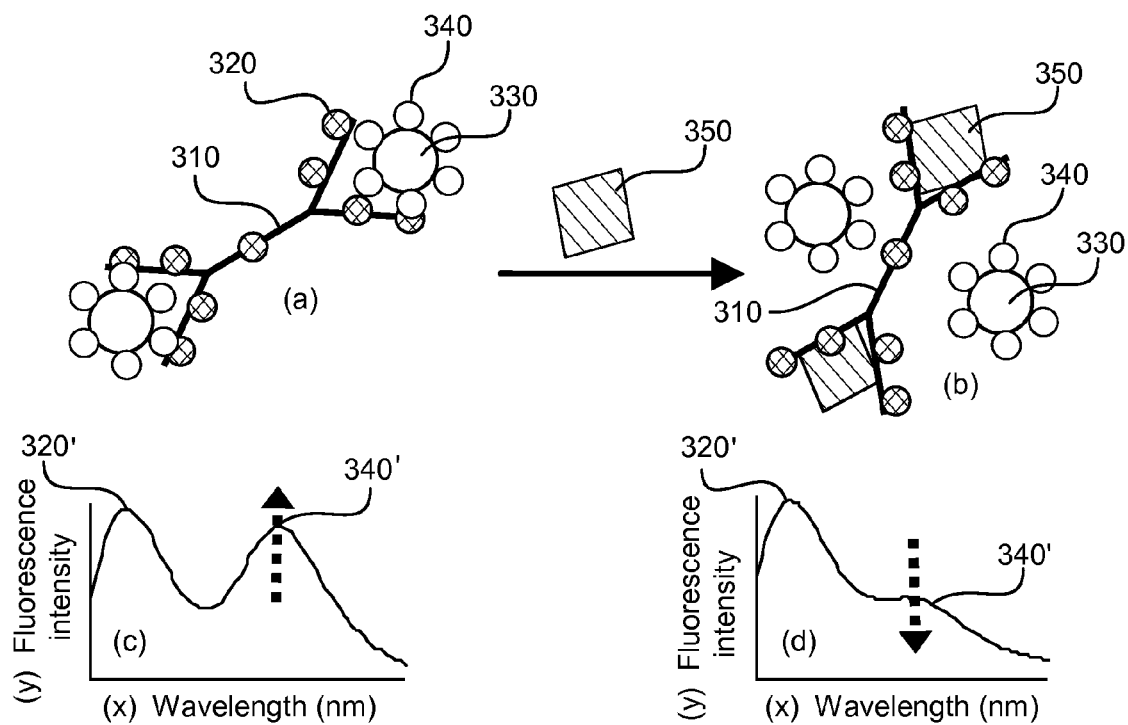
FIG. 3 represents a competitive binding reagent system.

While FIG. 3 shows the first fluorescent dye 320 being a donor and the second fluorescent dye 340 as an acceptor, the first dye 320 could be an acceptor and the second dye 340 a donor. Furthermore, although not shown in the figures, one of the dyes could be a quencher, which would result in a reduction of a single emission peak when the ligand 330 is associated with the receptor 310. Thus, in addition to donor/acceptor systems where two fluorescence peaks may be observed, in donor/quencher systems one peak is preferably observed.

Many fluorescent dyes may be used depending on the desired excitation and/or emission wavelength. In order to avoid the fluorescence from ISF, it is desirable that the wavelength of the donor/acceptor dyes be measured at greater than about 400 nm. Examples of suitable dyes include fluorescein isothiocyanate (FITC), trade secret compositions sold under the tradename ALEXA FLUOR® by Molecular Probes, Inc. (849 Pitchford Avenue, Eugene, Oreg. 97402-9165 USA), and cyan fluorescent protein/yellow fluorescent protein. Preferred dyes include the ALEXA FLUOR, with specific examples being Alexa Fluor 488 (AF488) and Alexa Fluor 555 (AF555), for example. Other preferred dyes include the cyanine dyes prepared with succinimidyl ester reactive groups, such as Cy-3, Cy-5, and Cy-5.5. The number immediately after the "Cy" indicates the number of bridge carbons. The number following the decimal point indicates a unique dye structure, which is determined by the substituents on the structure. Cy-3, Cy-5, and Cy-5.5 are available from GE Healthcare, Chalfont St. Giles, UK. Environmentally sensitive dyes, such as anilino-1-naphthalenesulfonic acid (ANS), which alter light in relation to polarity changes in the environment surrounding the dye, also are preferred.

Table IV, below, provides examples of suitable donor and corresponding acceptor dyes. The excitation (Exc) and emission (Emm) wavelengths of each dye are provided in nanometers. The excitation wavelength is the wavelength at which the dye absorbs the most light. The emission wavelength is the wavelength at which the dye gives off the most emitted light. The same dye may serve as a donor or acceptor, depending on the choice of the counterpart. For example, TRITC may serve as the acceptor for FITC, but as the donor for Alexa Fluor 647 (AF647). The greater the overlap between the emission wavelength of the donor and the excitation wavelength of the acceptor, the higher the energy transfer efficiency should be from the donor to the acceptor. Preferable donor and acceptor pairs have at least 60% energy transfer efficiency between the dyes, with more preferred pairs transferring at least 80%.

TABLE IV

| Donor (Exc/Emm) | Acceptor (Exc/Emm) |
| --- | --- |
| FITC (488/520) | TRITC (555/575) |
| TRITC (555/575) | AF647 (650/668) |
| TRITC (555/575) | AF660 (665/690) |
| FITC (488/520) | AF568 (578/602) |
| AF568 (578/602) | AF647 (650/668) |
| AF568 (578/602) | AF660 (665/690) |
| AF594 (594/618) | AF660 (665/690) |

TABLE IV-continued

| Donor (Exc/Emm) | Acceptor (Exc/Emm) |
|---|---|
| AF594 (594/618) | AF635 (635/648) |
| AF635 (635/648) | AF680 (682/705) |
| AF635 (635/648) | AF647 (647/667) |
| AF647 (647/667) | AF700 (695/720) |
| AF660 (665/690) | AF750 (750/772) |

Table V, below, provides presently favored pairs of donor and acceptor dyes.

TABLE V

| Donor (Exc/Emm) | Acceptor (Exc/Emm) |
|---|---|
| AF594 (594/618) | AF660 (665/690) |
| AF594 (594/618) | AF635 (635/648) |
| AF635 (635/648) | AF647 (647/667) |
| AF647 (647/667) | AF700 (695/720) |
| AF660 (665/690) | AF750 (750/772) |

Unlike FRET processes where both dyes emit, for donor/quencher systems the more efficient the resonance energy transfer between the donor and the quencher, the less light output is measured from the system. Thus, resonance energy transfer also may be measured using a fluorescent and a quenching dye as the donor and acceptor molecules, respectively. Any quenching dye may be used that adsorbs light from the donor and is compatible with the analysis. Examples of suitable quenching dyes include dabcyl chromophores and diarylrhodamine derivatives, such as those sold as QSY 7, QSY 9, and QSY 21 by Invitrogen, Carlsbad, Calif. Presently, the diarylrhodamine derivatives are preferred as quenching dyes. When a quenching dye is used, there will not be a substantial second fluorescent peak as a control, unless an additional control and/or reference dye is added to the analysis.

FIGS. 4(a) and 4(b) represent a binding reagent system using a conformational change to analyze for an analyte. FIG. 4(a) represents an analyte binding moiety (ABM) 410, such as a protein, having an attached first fluorescent dye 420 and an attached second fluorescent dye 440. In addition to proteins, the first and second fluorescent dyes 420, 440 may be attached to any molecule having the appropriate conformation and/or structural change upon binding the analyte. For example, the analyte binding moiety could be a glucose binding protein, hexokinase, glucokinase, apo-glucose oxidase, apo-glucose dehydrogenase, and the like. Preferably, the fluorescent dyes 420, 440 are covalently attached to the ABM 410 at specific sites to provide the desired fluorescent signal.

Figure 4:
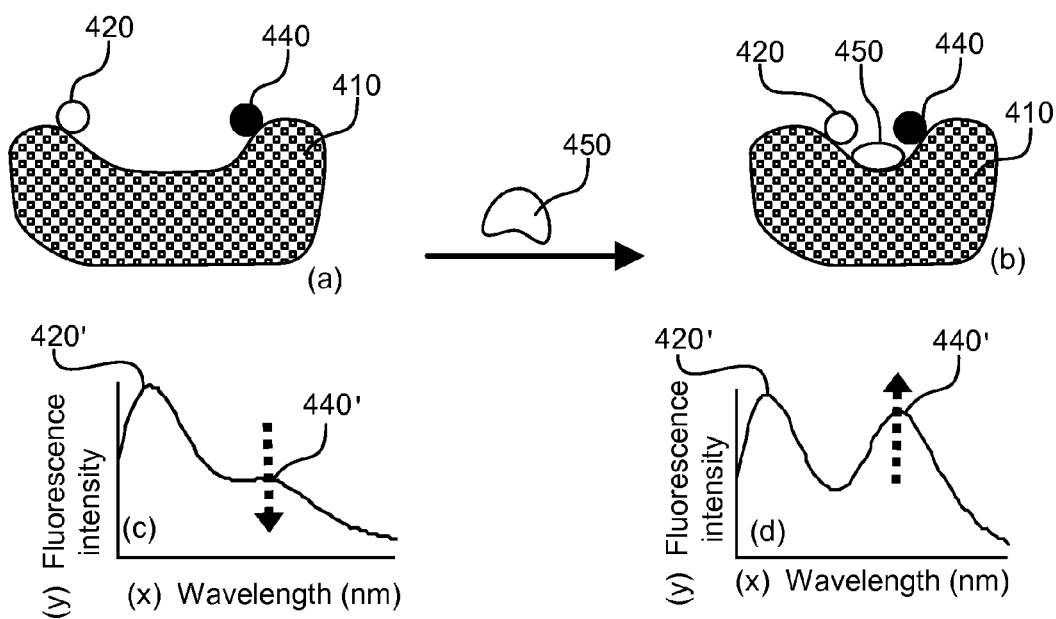
FIG. 4 represents an analyte binding reagent system.

As represented in FIG. 4(b), in the presence of the analyte 450, the ABM 410 binds the analyte 450, thus undergoing a conformational and/or structural change. FIG. 4(b) represents the ABM 410 undergoing a conformational change that brings the first and second fluorescent dyes 420, 440 in closer proximity. As shown in FIG. 4(c) and FIG. 4(d), as the dyes move closer together, a stronger fluorescence peak 440' is observed for the second fluorescent dye 440. While FIG. 4 represents a conformational change resulting in a decrease in the distance between the first and second fluorescent dyes 420, 440 in the presence of the analyte 450, the conformational change could result in an increase, thus providing a reduction in the fluorescence peak 440' observed for the second fluorescent dye 440 in the presence of the analyte 450. Thus, in the case of an increase in dye separation distance from the analyte-induced conformational change, the system would approximate a move from 4(d) to 4(c). Similarly, a structural change where the dyes were separated due to cleavage, ligation, and the like, would result in the system approximating a move from 4(d) to 4(c).

As the ABM assay of FIG. 4 and the competitive binding assay of FIG. 3 rely on a change in the distance between two fluorescent dyes, the dyes, donor/acceptor, donor/quencher, system response, and other spectroscopic concepts previously discussed for FIG. 3 may be generally applied to the ABM assay of FIG. 4. For glucose analysis, ABM reagent systems are preferably configured to detect glucose in ISF at least down to micromolar concentrations. By preferably configuring the dyes, dye ratio, and receptor/ligand ratio, the system can achieve a precision between different assays of ±5%, more preferably ±3%. At present, configurations providing a precision between different assays of ±0.5% are especially preferred.

Figure 5:
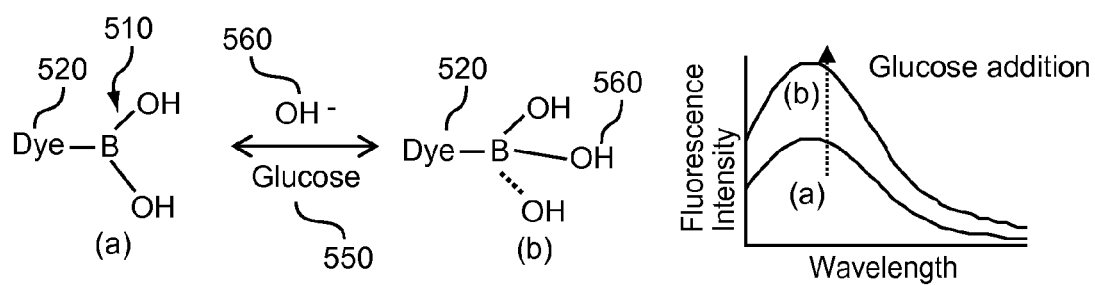
FIG. 5 represents a boronic acid glucose binding reagent system.

FIG. 5 represents a reagent system using a boronic acid 510 as the binding moiety. In the presence of glucose analyte 550, a hydroxyl group 560 transfers from the glucose molecule to the boronic acid 510, significantly reducing the electron withdrawing ability of the acid 510. A fluorescent dye 520 bonded to the acid 510 undergoes a change in fluorescence intensity and/or peak wavelength as the electron withdrawing ability of the acid 510 decreases. While not wishing to be bound by any particular theory, this change in fluorescence intensity is attributed to a photoinduced electron transfer (PET) mechanism. The graph shows the increase in fluorescence intensity when the boronic acid 510 is hydroxylated to form [Dye-B(OH$_2$)(glucose-OH)]$^-$, and is no longer an electron withdrawing group. Thus, as the glucose concentration of the sample increases, so does the observed fluorescence intensity from the dye.

Figure 6:
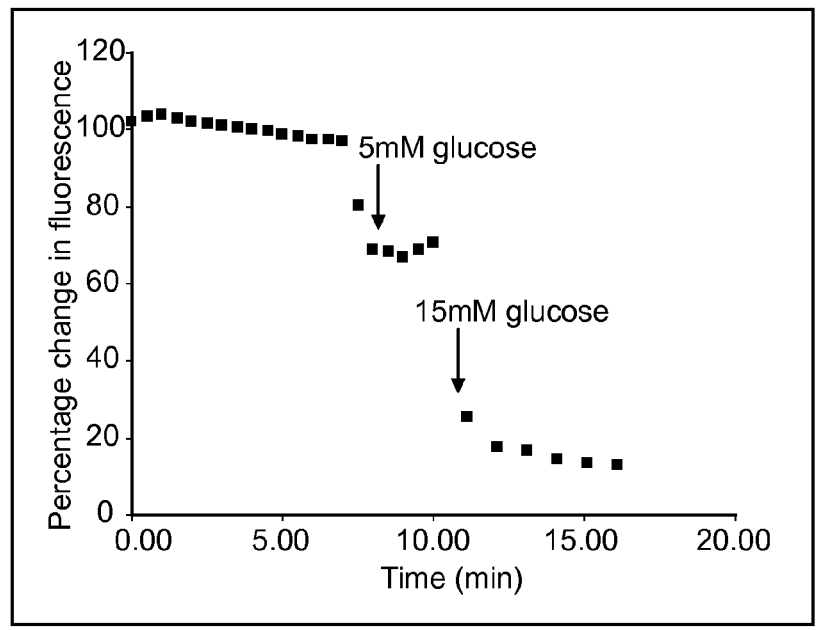
FIG. 6 plots percent change in fluorescence against analysis time for a sensor that includes a hydrogel.

FIG. 6 represents the fluorescence response to glucose as measured with an optical analysis system. The experimental configuration was a model for a hydrogel-based test sensor that includes an optical analyzer, as would be used in a transdermal optical analysis system. A mixture of 50 microliters of 2.5 micromolar GOx enzyme conjugated with FITC (FITC-GOx) was combined with 200 microliters of PBS buffer in a well of a transparent multi-well tray. A hydrogel was prepared as described above for FIG. 2B, but without the GOx enzyme, and was placed at the bottom of the well to account for any effect a gel material might have on the fluorescent response of the system. The mixture was continuously exposed to light having a wavelength of 485 nm from below the well, so that the gel was positioned between the light source and an optical detector. Glucose was added to the well after 7 minutes to provide a concentration in the well of 5 mM. Additional glucose was added to the well after 11 minutes to provide a concentration in the well of 15 mM.

The results of this analysis, plotted in FIG. 6, showed that a transdermal optical analysis system may analyze a sample as soon as sufficient analyte reaches the aqueous material, without an extended conditioning period. A stable fluorescence baseline was observed from the start of the analysis until the time the first aliquot of glucose was added at 7 minutes. After the fluorescence had changed in response to the glucose, a stable baseline was observed at the new fluorescence level. In addition, the changes in fluorescence upon addition of the aliquots of glucose were rapid, indicating that the system was capable of providing a measurable glucose response within 7 minutes from the start of the analysis. Thus, the analysis system containing a hydrogel did not provide a baseline signal that was unstable at the start of the analysis, which would have required an undesirable initial conditioning period before accurate readings could be obtained, as has been reported for conventional electrochemical transdermal systems.

Without being limited by any theory of operation, it is presently expected that incorporation of the enzyme reagent into the hydrogel, rather than in the surrounding liquid, would not significantly change the observed stability of the fluorescence baseline. While it is possible that incorporation of the enzyme reagent into the hydrogel may result in a lower rate of change in fluorescence when glucose is added, this would not be expected to result in the undesirable conditioning period typically required for electrochemical transdermal systems.

Figure 7A:
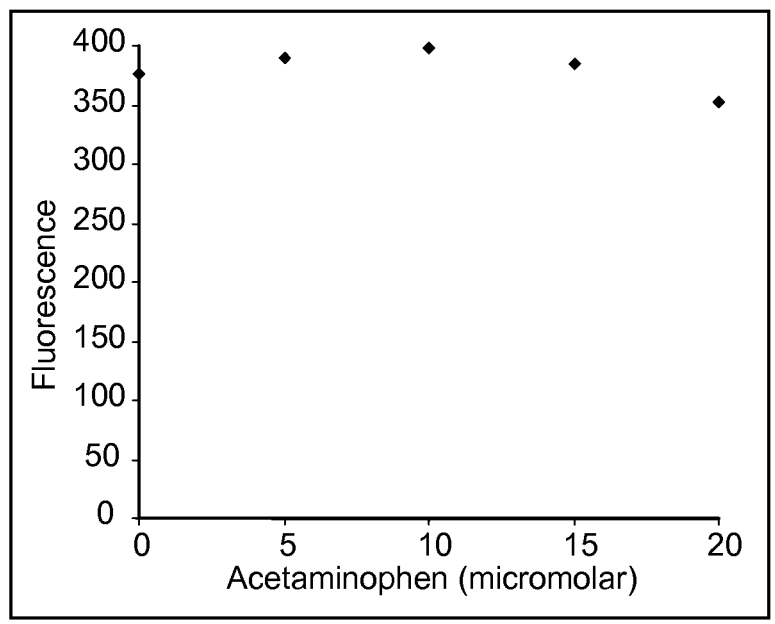
FIG. 7A plots difference in fluorescence against acetaminophen concentration for a sensor having optical detection.
Figure 7B:
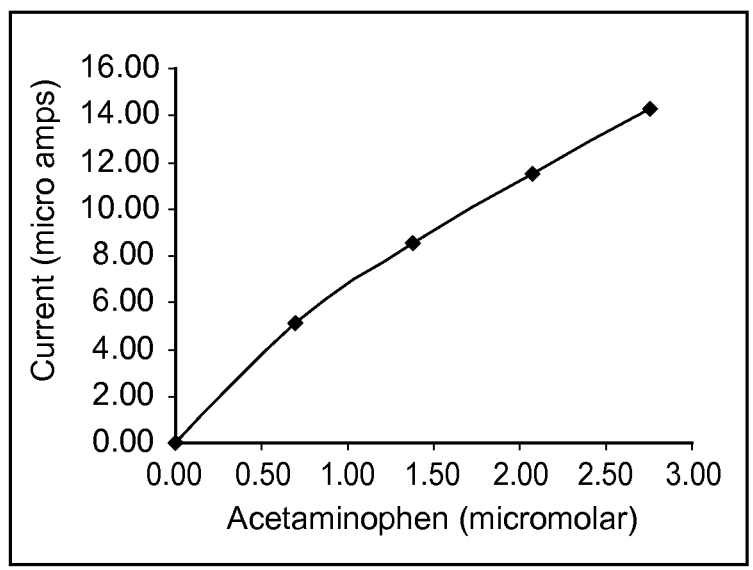
FIG. 7B plots electrical current against acetaminophen concentration for a sensor having electrochemical detection.

FIGS. 7A and 7B illustrate the difference between an optical analysis system and an electrochemical analysis system in their response to a common interferant for glucose. The electrochemical analysis system of FIG. 7B showed a change in the measured electrical current as the acetaminophen concentration was increased from 0 to 3 micromolar, and the electrical current was approximately proportional to the acetaminophen concentration. Thus, a sample containing both glucose and acetaminophen would produce a measured current having a contribution from both the glucose and the interferant. In contrast, the optical analysis system of FIG. 7A showed no substantial change in the measured fluorescence as the acetaminophen concentration was increased over an even wider range of 0 to 20 micromolar. Thus, a sample containing both glucose and acetaminophen would produce a change in fluorescence in response to the glucose, but not in response to the acetaminophen.

FIG. 7A plots the difference in fluorescence against acetaminophen concentration for a sensor having optical detection. A mixture of 50 microliters of 2.5 micromolar FITC-GOx with 200 microliters of PBS buffer was placed in a well of a transparent multi-well tray. A light source and detector were used to expose the mixture to light having a wavelength of 485 nm and to measure the resulting fluorescence from the mixture. After each addition of acetaminophen the mixture was exposed, and the fluorescence was measured. The change in fluorescence due to dilution alone was subtracted from the measured fluorescence values, to provide the fluorescence difference values plotted in FIG. 7A. The fluorescence difference did not change significantly as the acetaminophen concentration increased. Thus, acetaminophen should not act as an interferant during an analysis of glucose concentration with this type of optical sensor.

FIG. 7B plots electrical current against acetaminophen concentration for a sensor having electrochemical detection. A hydrogel containing GOx was prepared as described above for FIG. 2B. The gel and PBS buffer were placed in a well containing three screen printed electrodes. One electrode was a silver/silver chloride reference electrode, another electrode was a carbon counter electrode, and another electrode was a platinum/carbon working electrode. After 2 hours, a potential of 0.6 volts was applied continuously to the electrodes. After each addition of acetaminophen, the resulting electrical current was measured, as plotted in FIG. 7B. The amounts of acetaminophen in the well during the analysis were 0, 0.69, 1.38, 2.07 and 2.76 micromolar. The measured electrical current increased in a nearly linear fashion as the acetaminophen concentration increased. Thus, acetaminophen would act as an interferant during an analysis of glucose concentration with this type of electrochemical sensor.

Figure 8:
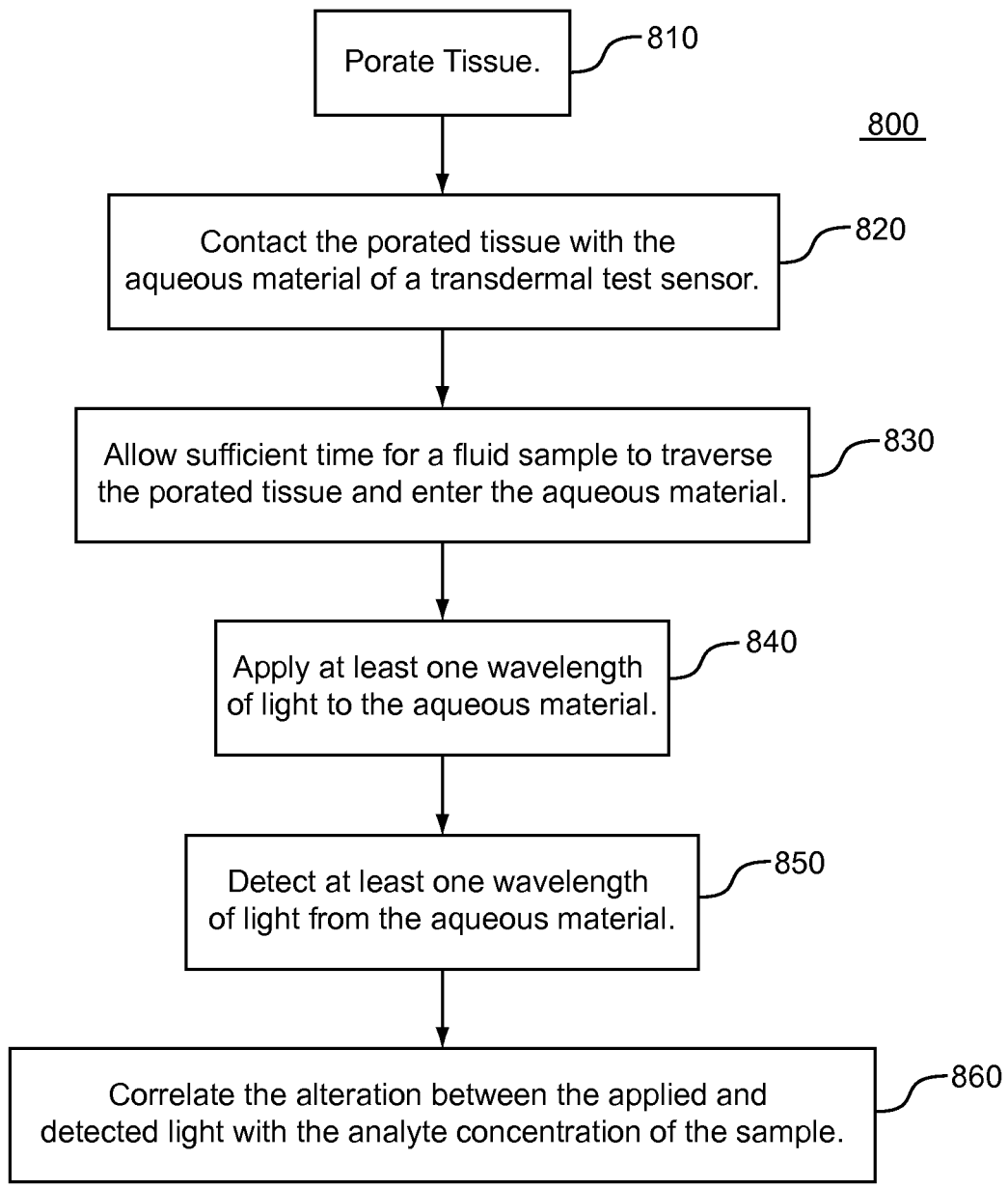
FIG. 8 depicts a method of determining the presence and/or concentration of an analyte in a fluid sample with a transdermal test sensor.

FIG. 8 depicts a non-invasive method 800 of determining the presence and/or concentration of an analyte in a fluid sample with a transdermal test sensor. In 810, a tissue is porated. Any poration technique may be used that provides the desired flow of analyte containing fluid to the test sensor. Examples of such techniques include ultrasonic processes, abrasion such as microneedle abrasion, laser ablation, and reverse iontophoresis.

In a preferred method, poration of tissue may be accomplished by ultrasonic processes, such as described in U.S. Patent Pub. Nos. 2004/0236268 and 2006/0094946. In this method, low-frequency ultrasonic waves increase the permeability of the tissue, presumably by disruption of the lipids in the stratum corneum, creating micropores. This transient disruption of the tissue has been shown to facilitate the non-invasive transdermal measurement of analytes without causing pain or significant adverse cutaneous effects (Kost, Nature Med., 6: 347-350 (2000)). Preferably, the device uses an ultrasonic horn with low frequency ultrasonic technology that, in addition to increasing permeability of the tissue, contains a microprocessor that automatically measures and records conductivity data. The microprocessor preferably performs on-line mathematical analysis of the conductivity and determines the best ultrasonic application duration to prevent unnecessary tissue irritation.

In another method, poration of tissue may be accomplished by microneedle abrasion, such as described in U.S. Pat. No. 6,835,184. In this method, a microabrader is positioned at a delivery site on the skin of a patient, where the microabrader has a support and a plurality of microneedles coupled to the support. Each of the microneedles has a length greater than the thickness of the stratum corneum, preferably from about 50 to 250 micrometers, and the microneedles may be arranged in an array of columns and rows and may be substantially uniformly spaced apart. The microabrader is moved across the tissue of the patient to allow the microneedles to penetrate into the stratum corneum substantially without piercing the stratum corneum. The movement of the microabrader across the skin abrades the stratum corneum at the delivery site to increase the permeability of the skin to ISF and/or an analyte in the ISF. The microabrader may be moved in a substantially straight line, and may be repositioned and moved across the skin one or more additional times.

In another method, poration of tissue may be accomplished by laser ablation, such as described in WO 2000/059371. In this method, an optical activation head is positioned on the surface of tissue, and optical energy such as laser radiation is applied to the surface of the tissue by the activation head. The applied optical energy heats the tissue and/or transfers heat by conduction to the tissue to ablate the tissue and form at least one opening in the tissue. Fluid such as ISF can then be collected from the tissue.

In another method, poration of tissue may be accomplished by reverse iontophoresis, such as described in U.S. Pat. No. 6,594,514. In this method, an iontophoretic sampling system, having one or more iontophoretic collection reservoirs in operative contact with an iontophoretic electrode, is placed in contact with tissue. The first iontophoretic electrode is operated as an iontophoretic cathode, the second iontophoretic electrode is operated as an iontophoretic anode, and substances such as ISF are actively extracted into the collection reservoir(s). The first iontophoretic electrode may then be operated as an anode, the second iontophoretic electrode may be operated as a cathode, and substances such as ISF again may be actively extracted into the collection reservoir(s). In addition, substances such as ISF that are passively extracted from the tissue are collected into another collection reservoir that is in contact with the tissue. Examples of passive collection reservoirs include skin patches and the like.

In 820, at least a portion of the porated tissue is contacted with the aqueous material of a transdermal test sensor, such as the test sensor 100 as previously discussed with regard to FIG.

1A and FIG. 1B. The test sensor may be held to the tissue with any adhesive or other method suitable for tissue use. In 830, sufficient time is allowed for a fluid sample to traverse the tissue porated in 810 and enter the aqueous material. In 840, at least one wavelength of light is applied to the aqueous material, and in 850 at least one wavelength of light from the aqueous material is detected. In 860, the alteration between the applied and detected light is correlated with the analyte concentration of the sample. The method 800 may include determining the concentration of one or more analytes in the fluid sample continuously or intermittently.

In 860, one or more correlation equations relating output signals, including the light alterations measured by the measurement device, and the concentrations of the analyte in the sample may be obtained by analyzing multiple samples having known analyte concentrations. The relationship determined between the known analyte concentrations and their corresponding output signals then may be used to determine experimental sample concentrations from output signals obtained from experimental samples.

Figure 9A:
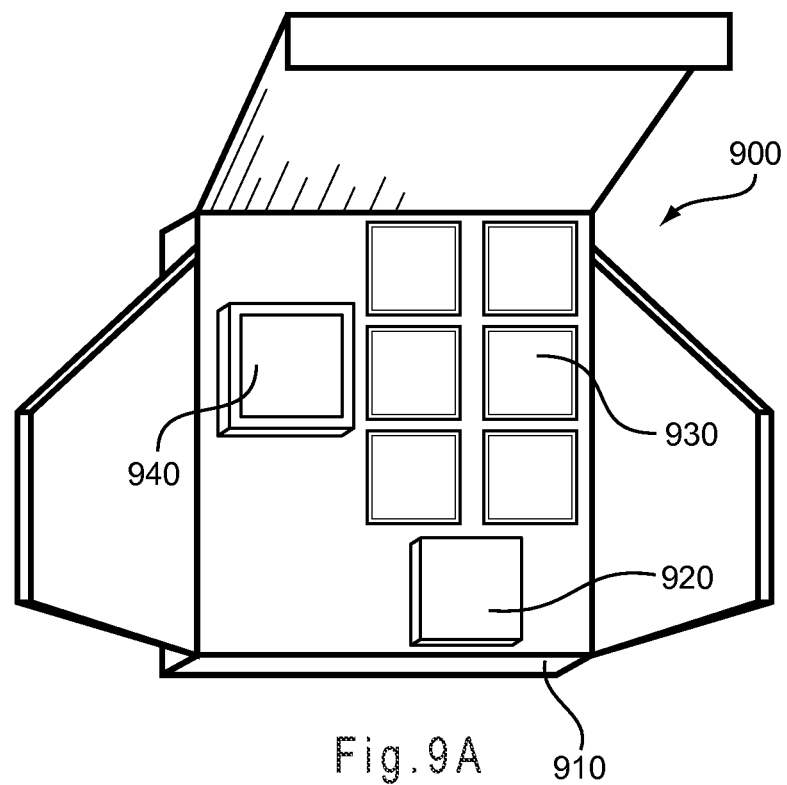
FIGS. 9A and 9B depict views of transdermal analyte analysis kits.
Figure 9B:
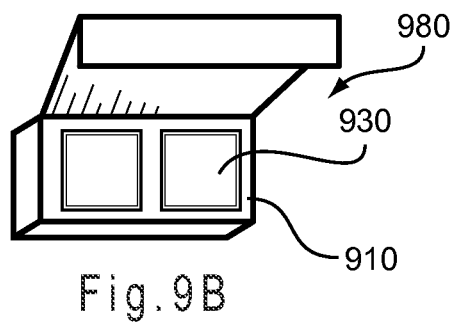

FIG. 9A and FIG. 9B depict views of transdermal analysis kits 900 and 980. The kit 900 may include an exterior package 910, one or more hydrogel elements 930, a housing 920 for the elements 930, and an electronic measurement device 940. The exterior package 910 may have paper and/or plastic components. The exterior package 910 may enclose multiple hydrogel elements, such as the elements 930, the electronic measurement device 940, and one or more supporting structures usually having paper and/or plastic components, instructions for use, and the like for the multiple test sensors and measurement device. The supporting structures may be formed from stiff paper, STYROFOAM™, and the like. The hydrogel elements 930 may be enclosed in paper, plastic, foil, MYLAR®, combinations thereof, and the like. As an example, the kit 980 of FIG. 9B may be considered as a refill for the kit 900 of FIG. 9A, thus including the hydrogel elements 930, but lacking the housing 920 and/or the electronic measurement device 940.

The hydrogel elements 930 may include an optical screen, and one or more adhesives, as previously discussed. Other components may be included with the hydrogel elements 930. While shown separately, the housing 920 may be integrated with the measurement device 940. If separate, the housing 920 may communicate through wires or wirelessly with the measurement device 940 to provide the desired functionality to the system.

Figure 10:
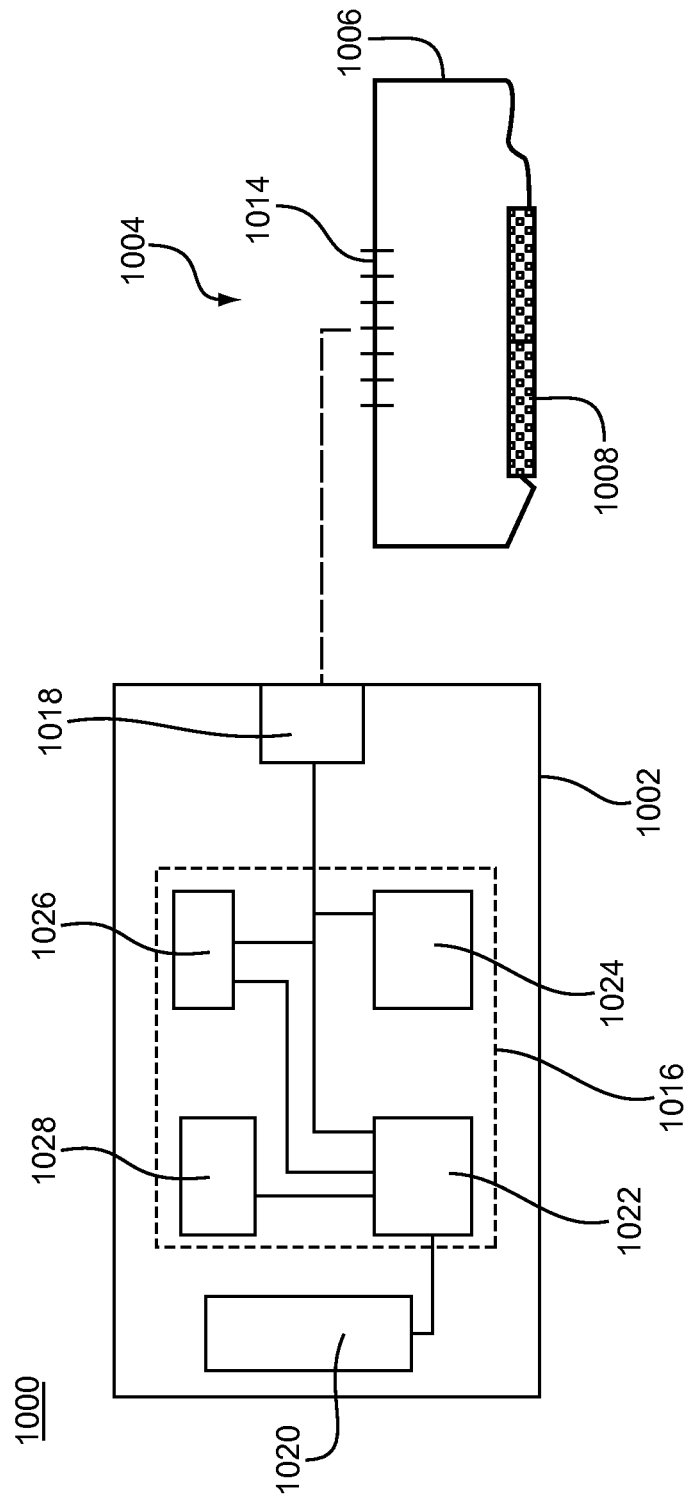
FIG. 10 depicts a schematic representation of a transdermal optical analysis system that determines an analyte concentration in a sample.

FIG. 10 depicts a schematic representation of a transdermal optical analysis system 1000 that determines an analyte concentration in a sample of a biological fluid. Transdermal system 1000 includes a measurement device 1002 and a test sensor 1004. The measurement device 1002 may be incorporated with the transdermal test sensor 1004, or it may be separate. When separate, the test sensor 1004 may be in constant or in intermittent communication with the measurement device 1002 through wires (including optical fibers) or wirelessly. Wirelessly includes by the transmission of light or other signal through air, tissue, and the like. An example of wireless transmission may be found in WO 2007/070586. The transdermal system 1000 may be utilized to determine analyte concentrations, including those of glucose, lactate, cholesterol, glutamate, and the like. The transdermal system 1000 may be used in clinical or home settings for detecting an analyte. While a particular configuration is shown, the transdermal system 1000 may have other configurations, including those with additional components.

The test sensor 1004 has a housing 1006 at least partially enclosing a aqueous material 1008. A reagent system may be deposited in the housing 1006 and/or the aqueous material 1008. The reagent system may include one or more enzymes, binding moieties, and like species. The reagent system may include one or more dyes capable of interacting with light. Light includes any suitable electromagnetic radiation from X-ray to infrared. The housing 1006 may have a sample interface 1014 with at least one optical portal or aperture for viewing the aqueous material 1008. The optical portal may be covered by an essentially transparent material. The sample interface 1014 may have optical portals on opposite sides of the housing 1006. The sample interface 1014 may be internal to the housing 1006 when the detector and/or light source are internal to the housing 1006.

The measurement device 1002 includes electrical circuitry 1016 connected to a sensor interface 1018 and a display 1020. The electrical circuitry 1016 includes a processor 1022 connected to a signal generator 1024, an optional temperature sensor 1026, and a storage medium 1028. The signal generator 1024 provides an electrical input signal to the sensor interface 1018 in response to the processor 1022. The electrical input signal may be used to operate or control the detector and light source in the sensor interface 1018. The signal generator 1024 also may record an output signal from the sensor interface as a generator-recorder. The sensor interface 1018 may be internal to the housing 1006 when the detector and/or light source are internal to the housing 1006.

The optional temperature sensor 1026 determines the temperature of the sample in the test sensor 1004. The temperature of the sample may be measured, calculated from the output signal, or assumed to be the same or similar to a measurement of the ambient temperature or the temperature of a device implementing the transdermal system. The temperature may be measured using a thermister, thermometer, or other temperature sensing device. Other techniques may be used to determine the sample temperature.

The storage medium 1028 may be a magnetic, optical, or semiconductor memory, another storage device, or the like. The storage medium 1028 may be a fixed memory device, a removable memory device, such as a memory card, remotely accessed, or the like.

The processor 1022 implements the analyte analysis and data treatment using computer readable software code and data stored in the storage medium 1028. The processor 1022 may start the analyte analysis in response to the presence of the test sensor 1004 at the sensor interface 1018, in response to user input, or the like. The processor 1022 directs the signal generator 1024 to provide the electrical input signal to the sensor interface 1018. The processor 1022 may receive the sample temperature from the temperature sensor 1026. The processor 1022 receives the output signal from the sensor interface 1018. The output signal is generated in response to the reaction of the analyte in the sample. The processor 1022 determines one or more analyte concentrations from the output signals using one or more correlation equation as previously discussed. The results of the analyte analysis may be output to the display 1020 and may be stored in the storage medium 1028.

The correlation equations between analyte concentrations and output signals may be represented graphically, mathematically, a combination thereof, or the like. The correlation equations may be represented by a program number (PNA) table, another look-up table, or the like that is stored in the storage medium 1028. Instructions regarding implementation of the analyte analysis may be provided by the computer readable software code stored in the storage medium 1028. The code may be object code or any other code describing or controlling the functionality described herein. The data from the analyte analysis may be subjected to one or more data treatments, including the determination of decay rates, K constants, ratios, and the like in the processor 1022.

In light-absorption and light-generated optical systems, the sensor interface 1018 includes a detector that collects and measures light. The detector may receive light from the test sensor 1004 through the optical portal in the sample interface 1014. The sensor interface 1018 also includes a light source such as a laser, laser diode, a light emitting diode, or the like. The incident beam may have a wavelength selected for absorption by the reaction product. The sensor interface 1018 directs an incident beam from the light source through the optical portal in the sample interface 1014. The detector may be positioned at an angle, such as 45° to the optical portal, to receive the light reflected back from the aqueous material 1008. The detector may be positioned adjacent to an optical portal on the other side of the aqueous material 1008 from the light source to receive light transmitted through the aqueous material 1008. The detector may be positioned in another location to receive reflected and/or transmitted light. Either the source and/or the detector may reside behind an optical screen or be embedded partially or wholly within the aqueous material 1008. The detector may include silicon, silicon avalanche, GaAs photodiodes, and like devices capable of converting light into electricity.

The display 1020 may be analog or digital. Display 1020 may be a LCD, a LED, a vacuum fluorescent, or other display adapted to show a numerical reading. Other displays may be used. The display 1020 electrically communicates with the processor 1022. The display 1020 may be separate from the measuring device 1002, such as when in wireless communication with the processor 1022. Alternatively, the display 1020 may be removed from the measuring device 1002, such as when the measuring device 1002 electrically communicates with a remote computing device, medication dosing pump, and the like.

In use, a liquid sample for analysis is transferred into the aqueous material 1008 through pores in a tissue, such as tissue. The liquid sample flows through the tissue and provides a pathway for the analyte to leave the tissue and enter the aqueous material 1008. The liquid sample reacts with the reagents present in the housing 1006 and/or the aqueous material 1008.

The test sensor 1004 is disposed adjacent or remote to the measurement device 1002. In either position, the sample interface 1014 is in optical communication with the sensor interface 1018. Optical communication includes the transfer of light between an optical portal in the sample interface 1014 and a detector in the sensor interface 1018. Optical communication also includes the transfer of light between an optical portal in the sample interface 1014 and a light source in the sensor interface 1018. Optical communication also includes the transfer of light between the aqueous material 1008 and the source and/or detector in the sensor interface 1018, when all or part of the sensor interface 1018 is within the housing 1006.

The processor 1022 may receive the sample temperature from the optional temperature sensor 1026. The processor 1022 directs the signal generator 1024 to provide an input signal to the sensor interface 1018. The sensor interface 1018 operates the detector and light source in response to the input signal. The processor 1022 receives the output signal generated from the detector in response to the analyte or analytes as previously discussed. The processor 1022 determines the analyte concentration of the sample from the alteration of one or more light intensities or wavelengths. The analyte concentration may be displayed on the display 1020 and/or stored for future reference.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A non-invasive method for determining a concentration of at least one analyte in a fluid, the method comprising:
   providing a transdermal test sensor including an aqueous material and a reagent system within the aqueous material, wherein the aqueous material is held between a top adhesive and a bottom adhesive within a volume defined by a semipermeable membrane and an additional membrane, the bottom adhesive adapted to adhere the test sensor to tissue, the test sensor further including an optical screen in contact with the additional membrane and the top adhesive and adapted to allow light communication with the aqueous material;
   contacting porated tissue with the semipermeable membrane of the transdermal test sensor;
   allowing sufficient time for the fluid sample to traverse to an external surface of the porated tissue and enter the aqueous material external to the porated tissue, the reagent system including at least one analyte selective reagent, at least one optically active moiety, and a reference dye;
   applying at least one wavelength of light to the aqueous material;
   detecting at least one wavelength of light from the aqueous material; and
   correlating an alteration of the applied light to the detected light with the concentration of the at least one analyte in the fluid sample.

2. The method of claim 1, wherein the at least one optically active moiety includes a pH sensitive dye.

3. The method of claim 1, wherein the analyte selective reagent includes at least one receptor and one or more species that the analyte displaces from the at least one receptor.

4. The method of claim 1, wherein the analyte selective reagent includes at least one analyte binding moiety that undergoes a conformation change when contacted by the analyte.

5. The method of claim 1, wherein the analyte selective reagent includes at least one analyte binding moiety that undergoes a change in electron withdrawing ability when contacted by the at least one analyte.

6. The method of claim 1, wherein the optically active moiety includes a donor fluorescent dye and an acceptor fluorescent dye.

7. The method of claim 6, wherein the concentration of the at least one analyte is correlated with a decrease in acceptor dye fluorescence in the presence of the at least one analyte as compared to the acceptor dye fluorescence in the absence of the at least one analyte.

8. The method of claim 1, wherein the optically active moiety includes a donor fluorescent dye and a quencher.

9. The method of claim 1, wherein the at least one analyte is selected from the group consisting of glucose, cholesterol, glutamate, lactate, and combinations thereof.

10. The method of claim 1, wherein the at least one analyte is glucose.

11. The method of claim 1, wherein two or more analytes are detected.

12. The method of claim 1, wherein the fluid sample is interstitial fluid.

13. The method of claim 1, wherein the correlating of the alteration of the applied light to the detected light with the concentration of the at least one analyte in the fluid sample is repeated at pre-selected time intervals.

14. The method of claim 13, the pre-selected time intervals are at least once every 20 minutes for at least 24 hours.

* * * * *